(12) United States Patent  (10) Patent No.: US 7,902,501 B2
Landgraf  (45) Date of Patent: Mar. 8, 2011

(54) ION MOBILITY SPECTROMETER AND METHOD FOR OPERATION

(75) Inventor: Jürgen Landgraf, Gutenberg (DE)

(73) Assignee: Bruker Daltonik GmbH, Bremen (DE)

( * ) Notice: Subject to any disclaimer, the term of this patent is extended or adjusted under 35 U.S.C. 154(b) by 179 days.

(21) Appl. No.: 12/266,113

(22) Filed: Nov. 6, 2008

(65) Prior Publication Data

US 2009/0114811 A1  May 7, 2009

(30) Foreign Application Priority Data

Nov. 6, 2007  (DE) .......................... 10 2007 052 802

(51) Int. Cl.
 *H01J 49/00* (2006.01)
 *B01D 59/44* (2006.01)
(52) U.S. Cl. ...... 250/288; 250/283; 250/284; 250/269.1; 422/50; 422/83
(58) Field of Classification Search .......... 250/281–284, 250/288, 269.1, 435, 438, 428; 422/50, 83, 422/98
See application file for complete search history.

(56) References Cited

U.S. PATENT DOCUMENTS

| 3,621,240 | A | * | 11/1971 | Cohen et al. ................. 250/282 |
| 3,699,333 | A | | 10/1972 | Cohen et al. |
| 4,311,669 | A | | 1/1982 | Spangler |
| 4,551,624 | A | | 11/1985 | Spangler et al. |
| 4,777,363 | A | | 10/1988 | Eiceman et al. |
| 5,109,691 | A | | 5/1992 | Corrigan et al. |
| 5,420,424 | A | | 5/1995 | Carnahan et al. |
| 5,683,741 | A | * | 11/1997 | Seng et al. ......................... 427/8 |
| 5,684,300 | A | * | 11/1997 | Taylor et al. ................. 250/286 |
| 5,723,861 | A | | 3/1998 | Carnahan et al. |
| 5,736,739 | A | | 4/1998 | Uber et al. |
| 5,763,876 | A | | 6/1998 | Pertinarides et al. |
| 5,811,059 | A | | 9/1998 | Genovese et al. |
| 5,968,837 | A | * | 10/1999 | Doring et al. ................. 436/173 |
| 6,627,878 | B1 | | 9/2003 | Machlonski et al. |
| 6,803,567 | B2 | | 10/2004 | Leonhardt et al. |
| 7,211,791 | B2 | | 5/2007 | Miller et al. |
| 7,511,268 | B2 | * | 3/2009 | Landgraf ....................... 250/288 |
| 7,547,880 | B2 | * | 6/2009 | Landgraf et al. .............. 250/287 |
| 7,579,589 | B2 | * | 8/2009 | Miller et al. .................. 250/292 |
| 2002/0016004 | A1 | | 2/2002 | Nguyen et al. |
| 2003/0036272 | A1 | | 2/2003 | Shamouilian et al. |
| 2005/0085740 | A1 | | 4/2005 | Davis et al. |
| 2005/0139762 | A1 | | 6/2005 | Miller et al. |
| 2006/0102844 | A1 | | 5/2006 | Sauer et al. |
| 2006/0192103 | A1 | * | 8/2006 | Landgraf ....................... 250/287 |
| 2006/0249673 | A1 | | 11/2006 | Breach et al. |
| 2009/0114812 | A1 | * | 5/2009 | Landgraf ....................... 250/282 |

FOREIGN PATENT DOCUMENTS

DE  19502674  9/1996

(Continued)

*Primary Examiner* — Bernard E Souw
(74) *Attorney, Agent, or Firm* — O'Shea Getz P.C.

(57) ABSTRACT

A method for operating an ion mobility spectrometer comprises supplying an analyte substance into a reaction chamber of an ion mobility spectrometer having a closed internal gas circuit and at least one membrane inlet having an inner membrane chamber, changing at least one of flow resistances and gas paths in the closed internal gas circuit, and controlling at least one of a quantity and a concentration of analyte-containing gas flowing from the inner membrane chamber to the reaction chamber.

20 Claims, 11 Drawing Sheets

FOREIGN PATENT DOCUMENTS

| | | |
|---|---|---|
| DE | 19938392 | 2/2001 |
| DE | 10254960 | 6/2004 |
| DE | 10310394 | 9/2004 |
| EP | 0774663 | 5/1997 |
| WO | 9306476 | 4/1993 |
| WO | 9738302 | 10/1997 |

* cited by examiner

ION MOBILITY SPECTROMETER AND METHOD FOR OPERATION

PRIORITY INFORMATION

This patent application claims priority from German patent application 10 2007 052 802.9 filed Nov. 6, 2007, which is hereby incorporated by reference.

FIELD OF THE INVENTION

The invention relates to an ion mobility spectrometer.

BACKGROUND OF THE INVENTION

Possibly dangerous substances, for example analyte substances, in ambient air are monitored in a large number of applications, such as environmental air analysis in nature or in buildings (e.g., inside chemical companies; for the detection of leaking poisons, chemical warfare agents (CWAs) or explosives). Ion mobility spectrometry is a method introduced in the 1970s for highly sensitive detection of polluting substances at low concentrations in air or other sample gases.

An ion mobility spectrometer (IMS) can be operated at ambient pressure. Ion mobility spectrometers are relatively compact and can be manufactured simply and inexpensively, which makes them particularly suitable for portable and mobile gas monitors and warning devices. Drift-time spectrometers are the most widely used ion mobility spectrometers. Other types of ion mobility spectrometers include, for example, the Aspiration Ion Mobility Spectrometer from the Finnish company Environics Oy and the Asymmetric Field Ion Mobility Spectrometer (FAIMS).

The analyte substances to be detected are usually ionized in a "reaction chamber". The drift-time IMS includes a measuring tube comprising the reaction chamber and a drift chamber. Ions generated in the reaction chamber, for example short ion pulses, are introduced into the drift chamber. The ion pulses move through the drift gas under the influence of an electric field. The ion pulses are separated in drift times according to their different drift velocities caused by their different mobilities. If the parameters of the drift gas, such as its temperature, humidity and pressure, are held constant, then the drift velocities of the ions are characteristic of the various substances.

In FAIMS devices, the ions are separated according to a dependency of their mobility on the field strength. The following description, however, will concentrate on drift-time ion mobility spectrometers. However, this restriction should not exclude the invention from being used by other types of ion mobility spectrometers.

In the majority of mobile ion mobility spectrometers, the gas is driven around in a closed internal gas circuit by a gas transporting device, such as a gas pump or a fan. A filter incorporated into the gas circuit removes moisture from the circulating gas and purifies it of analyte substances before it is returned again to the measuring tube of the ion mobility spectrometer. In particular, the temperature and humidity of the circulating gas are held constant within the closed gas circuit because these parameters strongly influence the sensitivity of the spectrometer.

The analyte substances which are to be detected in the sample gas may permeate into the gas circuit through a permeable membrane, on which the sample gas impinges from the outside. A membrane inlet usually consists of two chambers separated by the membrane, where the inner chamber is part of the closed internal gas circuit, and the outer chamber is part of an external gas circuit. The outer chamber is flooded through by the sample gas drawn in from a sampling location. Membranes made of organic polymers for example silicone rubber, may be used. The membranes are more permeable to the majority of organic analyte substances than water, thus reducing the unfavorable ingress of moisture into the gas circuit. A membrane inlet requires heating in order to reduce permeation delay and unwanted storage effects in the edges of the membrane where the material is clamped into a frame. In practice, the reaction of the measurement signal to a change in external concentration, in a number of low-volatility substances, may be delayed by several minutes at normal industry temperatures and membrane thicknesses.

Many commercially available ion mobility spectrometers that operate as stand-alone gas detectors incorporate a surge protection system. The circulation of the sample gas in the external gas circuit is interrupted if the measurement signal for a particular analyte substance exceeds a specified limit and the outer side of the membrane is purged with filtered air. Due to the time delays in the membrane inlet, when substance concentrations are high, the membrane and the surfaces in the inlet area of the internal gas circuit are already heavily exposed to the analyte substance before the high concentration is detected in the measuring tube and the surge protection is triggered. As a result, quantities of analyte substance that have already passed through the membrane into the gas circuit, or are still stored in the membrane, still reach the measuring tube even after the surge protection has been triggered. Unheated surfaces in the inlet region of the measuring tube are therefore significantly exposed to the analyte substances and the measurement signals remain saturated for a period of time, known as a dead time. During the dead time, the ion mobility spectrometer is no longer able to perform its warning function nor able to detect other analyte substances. The dead times caused by excessive analyte substance concentrations in the measuring tube may often be significantly longer than the time required to purge the heated membrane. If the concentration of analyte substance is still high enough, the cycle of purging and measurement is repeated, in some examples several times, until the substance concentration has dropped sufficiently.

Ion mobility spectrometers of the prior art have a relatively low dynamic measuring range that is determined by the design and operating parameters of the measuring tube. It is not realistically possible for these parameters to be modified during operation to match changed measuring conditions. It is, however, known that the measuring range of an ion mobility spectrometer can be extended to encompass high substance concentrations where the gas sample drawn in is diluted with a measured quantity of purified air or other gas before it reaches the permeable membrane. When the dilution ratio is changed, it is necessary to allow a settling time to elapse after the change before the measurement signal stabilizes due to the time delays from the membrane inlet. During the settling time, the ion mobility spectrometer does not yield any reliable results.

Commercially available ion mobility spectrometers are also known that monitor the air from several sampling locations synchronously using a single measuring tube. It is often desirable to monitor the gas from several sampling locations in order to reduce the expense and number of devices employed. For example, several inlet lines, usually heated, are used to feed sample gas from the various sampling locations. The gas flowing from the sampling locations are cyclically connected to a single membrane inlet via switching valves. To obtain reproducible measurements, it is necessary, when switching between two sampling locations, to wait until the measurement signal from the previous sampling location has fully decayed and the analyte substances from the following sampling location have permeated the membrane. The sluggishness of the membrane inlet results in relatively long cycle times which seriously restrict the usefulness of such a method.

SUMMARY OF THE INVENTION

A method for operating an ion mobility spectrometer comprises supplying an analyte substance into a reaction chamber of an ion mobility spectrometer having a closed internal gas circuit and at least one membrane inlet having an inner membrane chamber, changing at least one of flow resistances and gas paths in the closed internal gas circuit, and controlling at least one of a quantity and a concentration of analyte-containing gas flowing from the inner membrane chamber to the reaction chamber.

One method of controlling the quantity of circulating gas having analyte substances that flows into the measuring tube during a metering phase and/or an isolation phase, is to periodically reverse the flow into the measuring tube by switching valves in a suitably designed internal gas circuit.

A second method reduces the flow of analyte-containing gas into the measuring tube through switchable by-passes. This may reduce the amount of analyte substances flowing through the reaction chamber and may avoid over-saturation. A related method mixes the analyte-containing gas flow with purified gas shortly before entering the reaction chamber, thus diluting the analyte substance and decreasing its concentration.

A third method switches gas flows from two membrane inlets of very different permeability to reduce sensitivity.

A fourth method guides the gas flow inside the reaction chamber on different paths, thus controlling the exposure of analyte substance molecules to protonating reactant ions.

With two or more membrane inlets, sample gas from several sampling locations may be cyclically measured independently from each other without excessive waiting times. As in the first method described above, reversing the flow may help to control over-saturation.

The controllable flow elements and switching elements in an ion mobility spectrometer according to the disclosure may be arranged such that analyte-containing circulating gas does not flow through them, or are positioned in a gas path of the gas circuit that leads away from the measuring tube.

These and other objects, features and advantages of the present invention will become more apparent in light of the following detailed description of preferred embodiments thereof, as illustrated in the accompanying drawings.

DETAILED DESCRIPTION

A drift-time ion mobility spectrometer comprises a measuring tube 10 that includes a reaction chamber 11 and a drift chamber 12, separated by a gating grid 13. Primary ionization of gas molecules occurs inside the reaction chamber 11 close to a radiation source 14. In one example, the radiation source 14 includes a radioactive beta emitter, for example $^{63}$Ni. The primary ions undergo chain reactions with water and other gas molecules, forming complex reactant ions which ionize analyte substance molecules by protonation. A quantity of gas possibly containing analyte substances is fed by an internal gas circuit into the reaction chamber 11, where the analyte molecules are ionized by the reactant ions. Residual reactant ions and freshly created analyte ions drift toward the gating grid 13 under the influence of an electric field. Analyte and reactant ions are released in short pulses into the drift chamber 12 by briefly opening the electrical grating grid 13, where the ions move in an axial electric field towards the collecting electrode 15. The substance-specific drift velocities separate ions of different mobilities in space and time and create a time-dependent current to be measured as an ion mobility spectrum at a collecting electrode 15. Evaluation of the ion mobility spectrum, for example by software programs in an accompanying computer, reveals the presence and eventually the concentration of the different analyte substances under investigation.

The supply of analyte substances is provided by a membrane inlet 21 comprising two chambers 21a, 21b separated from one another by a heated, permeable membrane 21c. The sample gas is drawn in from the gas inlet 23 by an external pump 20. The gas flows past the heated membrane 21c to the gas outlet 24. A proportion of the analyte substances in the sample gas enters the internal gas circuit by permeating through the membrane 21c.

In one example, a closed internal gas circuit comprises a pumping device 30 for circulating the gas, a filter 40 to clean the gas of moisture and residual analyte substances, the inner chamber 21b of the membrane inlet 21 delivering the analyte substances, and the measuring tube 10 with reaction chamber 11 and drift tube 12. The filter, for example, permanently holds the humidity of the circulating gas below 100 ppm (parts per million), for example at around 10 ppm. In the drift chamber 12, cleaned circulating gas flows from the collecting electrode 15 to the gating grid 13, moving in the opposite direction to the drift of the ions. This prevents analyte-containing gas from passing from the reaction chamber 11 into the drift chamber 12. Additionally, penetrating substances may be ionized for the first time or react with existing ions and thereby falsify the analytical results.

Generally, there are two types of ion mobility spectrometers: those responding with output signals proportional to substance amounts and those which respond proportional to substance concentrations. Where essentially all substance molecules are ionized inside the reaction chamber, the output is proportional to the total number of substance molecules fed into the reaction chamber. Increasing the gas velocity increases the output signal because more molecules are fed into the reaction chamber. Where, in contrast, the chance for a substance molecule to be ionized is dependent on the residence time inside the reaction chamber, the responding output signal is concentration-proportional. The gas velocity does not influence the signal because a higher number of substance molecules brought into the reaction chamber by a higher gas velocity is compensated by a shorter residence time. Although most ion mobility spectrometers are the concentration-proportional type, the following description predominantly relates to amount-proportional ion mobility spectrometers. However, those skilled in the art of ion mobility spectrometry can easily adapt the circuitry where a reduction of the concentration is required instead of a reduction of the amount of substance.

In one example, the spectrometer adapts the measuring range to the concentration of analyte substances in the external sample gas flow by additionally introducing valves 50, 60, 71, 72, 80, controllable throttles 90, and numerous gas restrictions into the internal gas circuit to reduce, reverse and/or dilute the internal analyte-containing gas flow into the reaction chamber 11. The adaptation is performed by feed-back control from the analytical results.

In a first embodiment, to control the quantity of circulating gas with analyte substances that flows into the measuring tube, the flow into the measuring tube periodically reverses by switching valves in a suitably designed internal gas circuit. The periodic reversal constitutes a metering phase and an isolation phase of a measurement method.

Figure 1A:
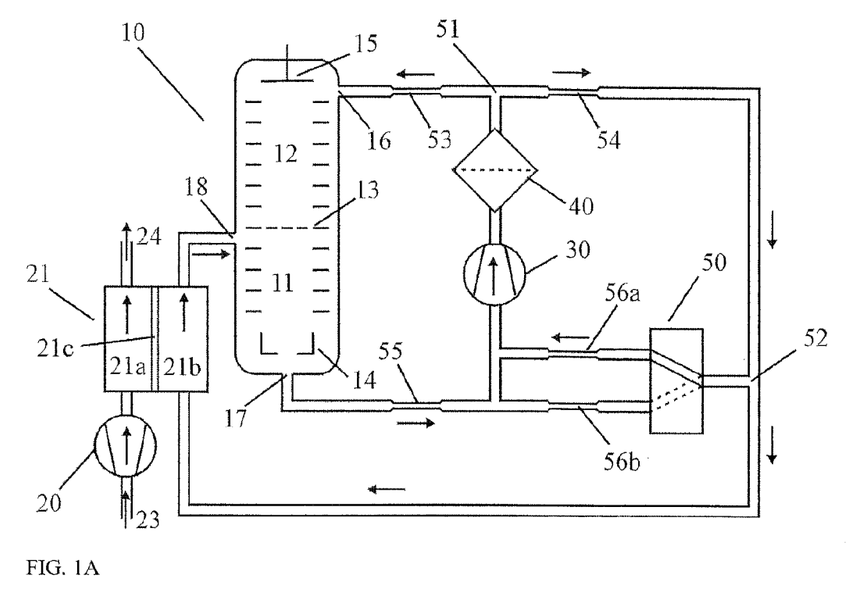
FIGS. 1A and 1B illustrate one embodiment of an ion mobility spectrometer configured to have a reversible flow of analyte-containing gas.
Figure 1B:
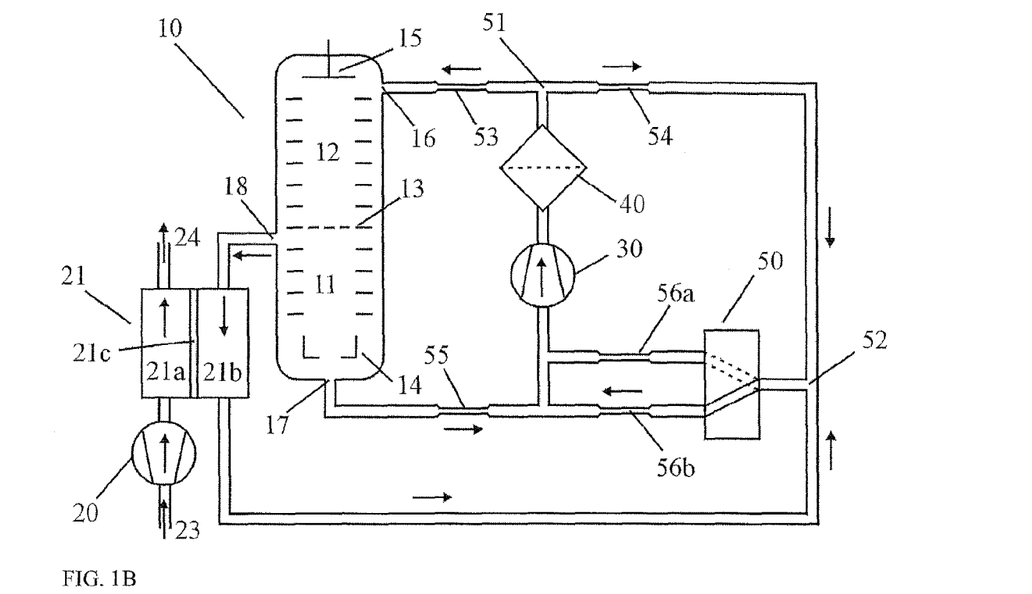

FIGS. 1A and 1B illustrate the two phases of the measurement method. Within the ion mobility spectrometer, the circulating gas that has been cleaned in the filter 40 is divided at the branching point 51, flowing partially into the drift chamber 12 and partially into the center connection of the changeover valve 50. Depending on the setting of the changeover valve 50, circulating gas is transported from the center connection back to the gas pump 30 either through the high resistance restriction 56a or the low resistance restriction 56b. Circulating gas is drawn out of the reaction chamber 11 through the gas connection 17 and flows to the gas pump 30.

The five flow restrictions 53, 54, 55, 56a and 56b of the internal gas circuit are arranged in the form of a bridge circuit. One of the two parallel branches of the bridge circuit includes the flow elements 53 and 55, where the measuring tube 10 is positioned between them. The second parallel branch includes the flow restriction 54 and, depending on the switching status of the changeover valve 50, either the restriction 56a with high resistance or the restriction 56b with low resistance. Cleaned circulating gas is supplied to the bridge circuit through the branching point 51. The diagonal branch of the bridge circuit passes from the gas connection 18 to the branching point 52 through the membrane inlet 21. The flow resistances of the five flow elements 53, 54, 55, 56a and 56b determines the direction of flow of the circulating gas in the diagonal branch and thereby in the inner chamber 21a of the membrane inlet 21.

In FIG. 1A, the membrane inlet 21 is in metering mode, whereas in FIG. 1B, the membrane inlet 21 is switched into isolation mode.

The time necessary to interrupt the supply of analyte-containing circulating gas to the measuring tube 10 depends on how quickly the flow direction in the branch of the bridge with the membrane inlet 21 can be reversed. Switching between the two operating modes is not affected by the sluggishness of the membrane inlet 21, nor by the residence time of the substances in the permeable membrane 21c.

In order to monitor ambient air, the measured concentrations of selected analyte substances are, for example, automatically compared with specified limits. If the concentration of a substance exceeds the specified limit, the ion mobility spectrometer is switched from the metering mode into the isolation mode using the changeover valve 50.

In isolation mode, no analyte-containing circulating gas enters the measuring tube 10. The analyte-containing circulating gas flows through the changeover valve 50, exposing the valve to large quantities of substance. Upon returning to the metering mode, cleaned circulating gas flows through the valve in the same direction. In the present example, it is not possible to reverse the flow of substances stored in the changeover valve 50. Therefore, an economical implementation with materials that do not necessarily guarantee low-reaction properties can be used.

Figure 2A:
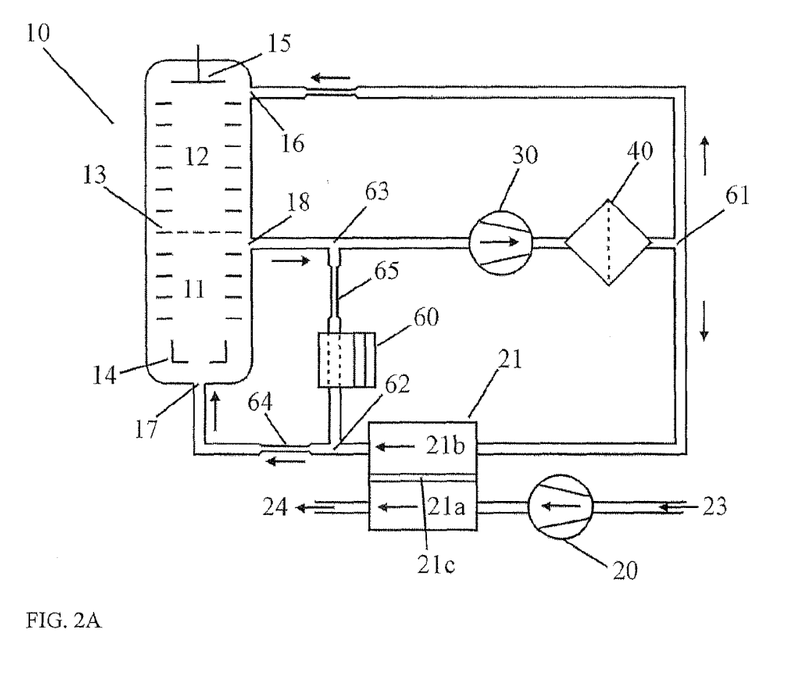
FIGS. 2A and 2B illustrate a second embodiment of the ion mobility spectrometer having a switchable by-pass.
Figure 2B:
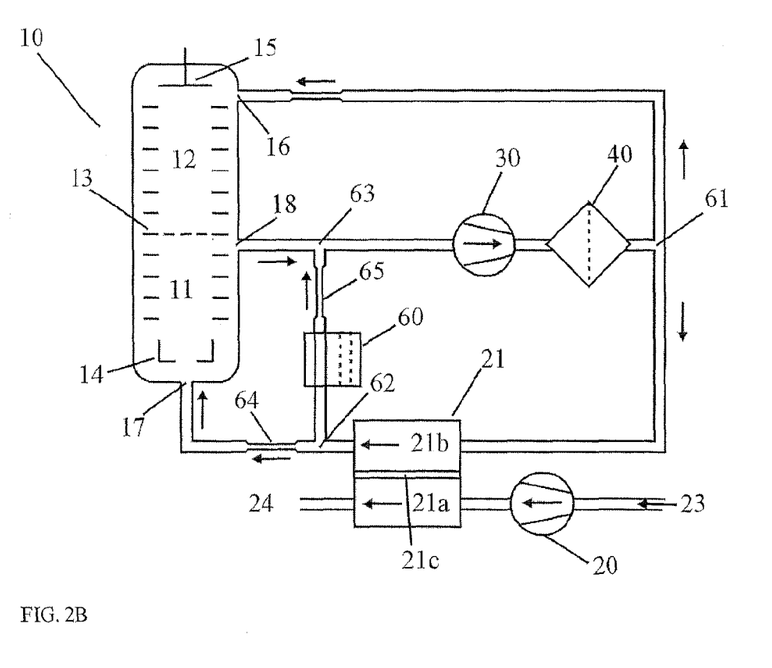

In a second embodiment illustrated in FIGS. 2A and 2B, a controllable by-pass causes a reduction of the analyte-containing gas flow into the measuring tube 10. The operation of a switching valve 60 in connection with a restriction 65 allows the quantity of analyte-containing circulating gas flowing into the reaction chamber 11 to be reduced in order to adapt the measuring range of the ion mobility spectrometer to high substance concentrations at a sampling location.

The analyte-containing circulating gas flowing from the membrane inlet 21 is divided between the two parallel branches through the measuring tube 10 and through the switching valve 60. The ratio of the gas flow in the two branches is inversely proportional to the flow resistances. For example, where the flow resistance 65 of the side branch through the switching valve 60 is only $\frac{1}{9}$ of the flow resistance 64 of the other branch through the reaction chamber 11, then only $\frac{1}{10}$ of the analyte-containing circulating gas enters the measuring tube 10. The remaining $\frac{9}{10}$ of the analyte-containing circulating gas flows directly through the gas pump 30 to the filter 40, where the substances are trapped. The measuring sensitivity is reduced to $\frac{1}{10}$ of the sensitivity in the operating mode with the switching valve 60 in the opposite state. Therefore, the ion mobility spectrometer has two different measuring ranges, covering a wide range of concentrations.

The time to switch between the two measuring ranges depends on the settling time of the gas flows in the gas circuit after switching the valve 60 and on the time for purging the gas channels between the membrane inlet 21 and the reaction chamber 11 that have come into contact with the sample. The time to switch between the measuring ranges is not affected by the sluggishness of the membrane inlet 21 nor by the residence time of the substances within the permeable membrane 21c. The permeation equilibrium is not disturbed by the switchover.

In contrast with the previous embodiment, the ion mobility spectrometer continues to operate with reduced sensitivity in the presence of high substance concentrations. Therefore, a reduction in the concentration of the monitored substances may be quickly detected, and the ion mobility spectrometer may be returned, for example automatically, to the high-sensitivity mode. As a result, the time required to restore operational readiness following excessive substance concentration is greatly reduced.

Using an electrically controlled, variable throttle valve instead of the switching valve 60 and the flow restriction 65, it is possible to continuously adjust or reduce the measuring range and measuring sensitivity, where the measurement signal for an analyte substance exceeds a specified limit. Where the throttle valve is calibrated, the measuring range can be automatically adapted according to the actual concentrations of the substances being monitored without losing the quantitative relationship between the measurement signal and the substance concentrations.

The method reduces the amount of analyte substances flowing into the reaction chamber 11, but not its concentration within the gas. For a concentration-proportional instrument, mixing the analyte-containing gas flow with purified gas shortly before entering the reaction chamber dilutes the analyte substance and decreases its concentration. The purified gas can be added with, for example, constant flow or a flow compensating the subtracting flow through the by-pass.

Figure 3A:
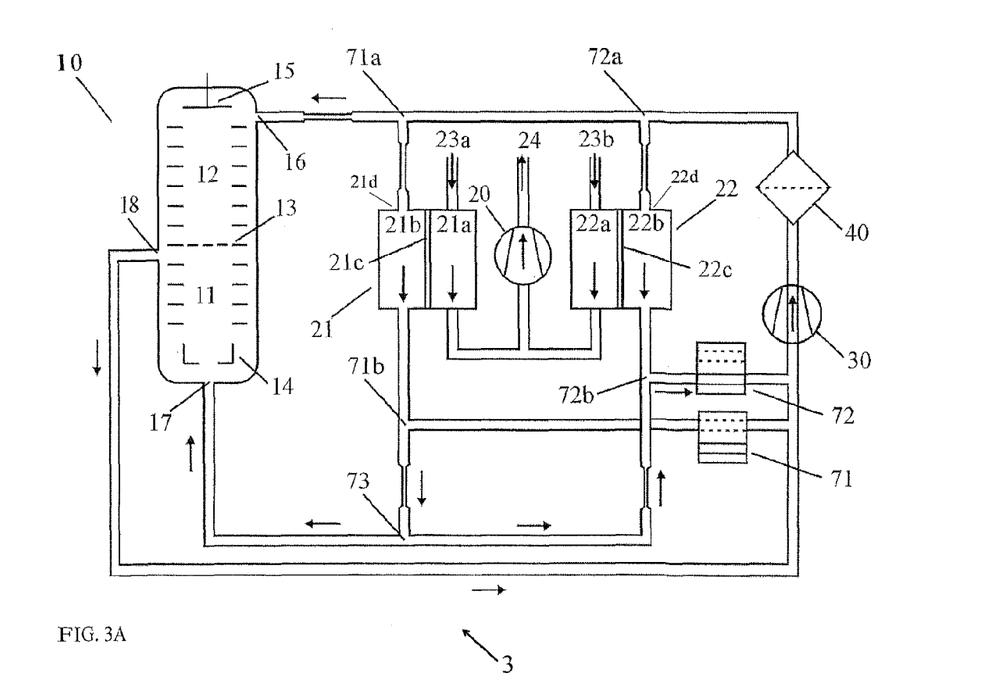
FIGS. 3A to 3C illustrate a third embodiment of the ion mobility spectrometer configured to independently monitor samples from two sampling locations.
Figure 3B:
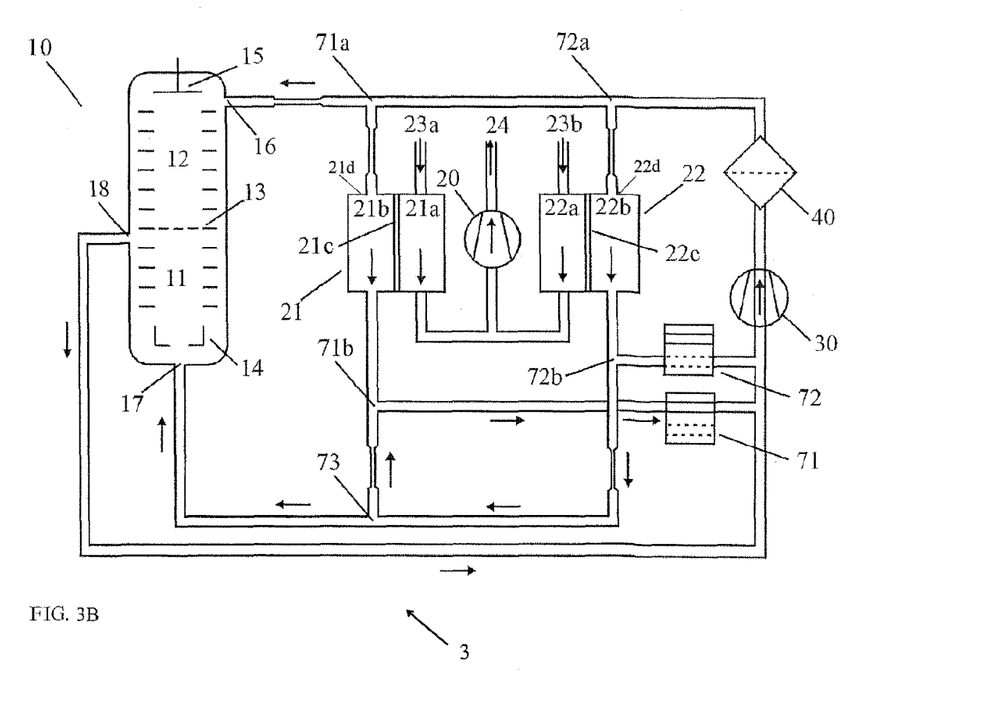
Figure 3C:
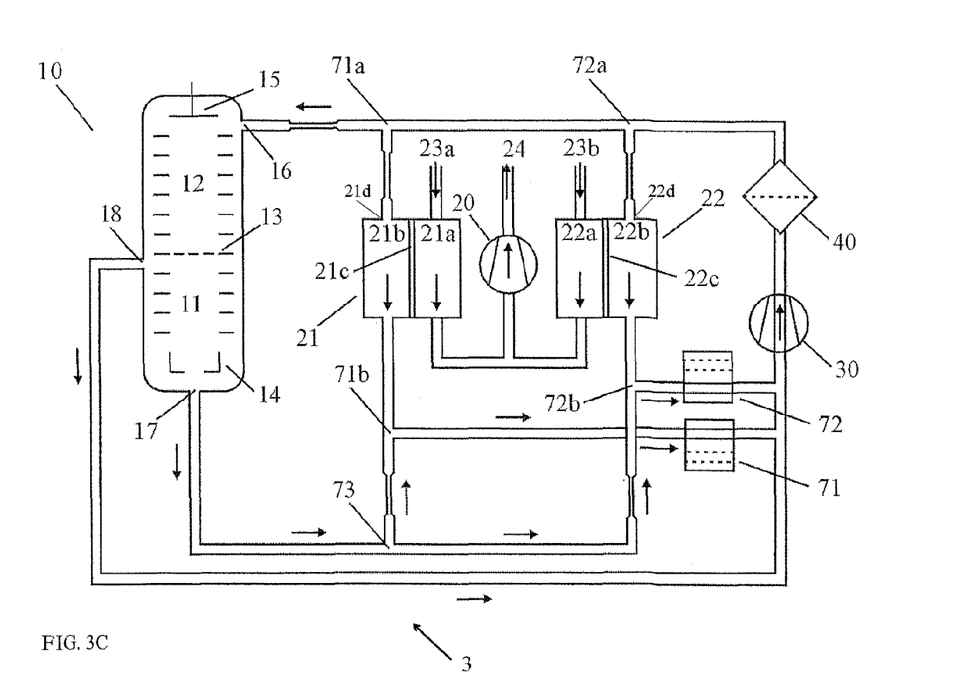

A third embodiment in FIGS. 3A and 3B illustrates two membrane inlets 21, 22 and two switching valves 71, 72 used to cyclically measure a sample gas from two different sampling locations 23a, 23b. The sample locations 23a, 23b can be cyclically measured independently from each other without excessive waiting times for membrane penetration balances. In case of high concentrations in both membrane inlets, reversing the flow to the reaction chamber 11 prevents over-saturation, as illustrated in FIG. 3C, similarly to the first embodiment described above.

The circulating gas cleaned in a filter 40 is divided at two branching points 71a, 72a and flows partially into the drift chamber 12 and partially into the two parallel membrane inlets 21, 22. The two membrane inlets 21, 22 each comprise an outer chamber 21a, 22a and an inner chamber 21b, 22b. The outer chamber 21a, 22a and the inner chamber 21b, 22b are separated by a heated permeable membrane 21c, 22c. The sample gas from the two sampling locations is drawn in through the two gas inlets 23a, 23b, using an external pump 20, and flows past the two heated membranes 21c, 22c to a common gas outlet 24. As a result, the sample gas from the relevant sampling location impinges continuously on the membranes 21c, 22c.

The two switching valves 71, 72 enable switching between the membrane inlets 21, 22 and therefore between the gas inlets 23a, 23b of the connected sampling locations. Thus, one membrane inlet contributes to the measurement signal, while the other membrane inlet is isolated from the measuring tube 10. In both switched states, cleaned circulating gas flows over the surfaces of the two membrane inlets 21, 22 on the circuit side to prevent, even in the inactive state, saturation of the membranes 21c, 22c and of the circulating gas in the inner chambers 21b, 22b.

In prior art ion mobility spectrometers configured to sample at different sampling locations, the gas inlets are connected one after another to the outer chamber of a single membrane inlet. To obtain reproducible results, it is necessary in each switching position to wait for both the measurement signal from the previous sampling location to fully decay and for the substances from the next sampling location to permeate the membrane. This results in relatively long cycle times, which severely limits possible applications.

In contrast, according to the embodiment illustrated in FIGS. 3A and 3B, gas inlet lines 21d and 22d are each connected to separate membrane inlets 21 and 22, respectively. Substances may pass continuously through the membranes 21c, 22c, without any interruption in both the active and the inactive switch settings. The time to switch between the two membrane inlets 21, 22 is independent of the storage or permeation times of the membranes 21c, 22c. In some examples, the switching time is only limited by the settling time of the internal gas flows. In other examples, the switching time is additionally limited by the adsorption effects on the surfaces of the branches of the internal gas circuit that come into contact with substance. The changes in concentration at two different sampling locations can be sampled almost synchronously by switching between the two membrane inlets 21, 22.

FIG. 3C illustrates another example of an operating state of the ion mobility spectrometer. The switching valves 71, 72 are both open and thereby connect both branching points 71b and 72b to the suction side of the gas pump 30. The membrane inlets 21, 22 are both in isolation mode. As a result, the direction of flow reverses in the branch between the gas connection 17 and the branching point 73, and circulating gas is sucked out of the gas connections 17 and 18. Therefore, the ion mobility spectrometer 3 may be switched fully into isolation mode when excessive substance concentrations are present at both sampling locations.

Figure 4A:
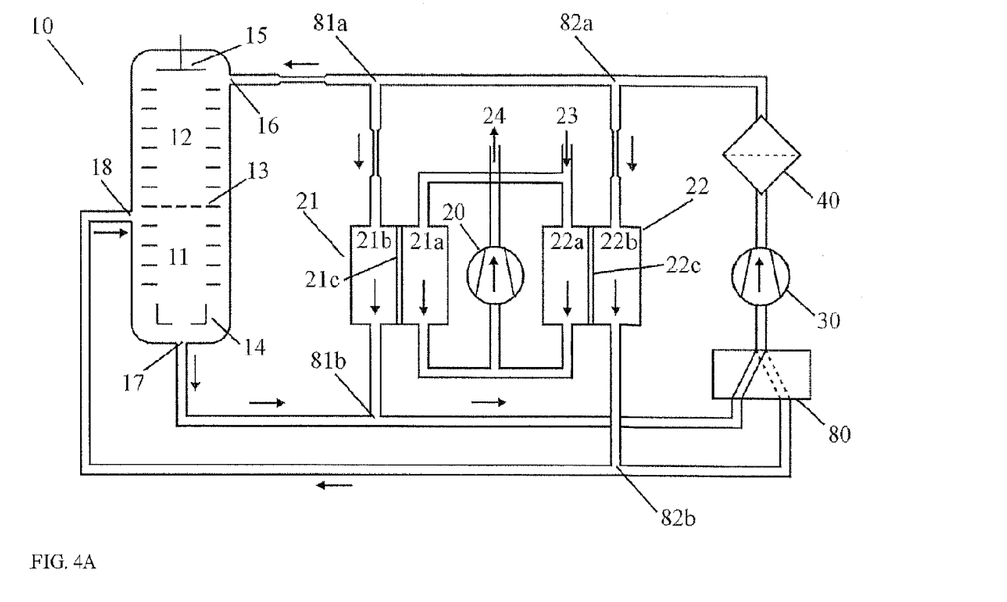
FIGS. 4A and 4B illustrate a fourth embodiment of the ion mobility spectrometer configured to adapt the sensitivity to the analyte substance concentration.
Figure 4B:
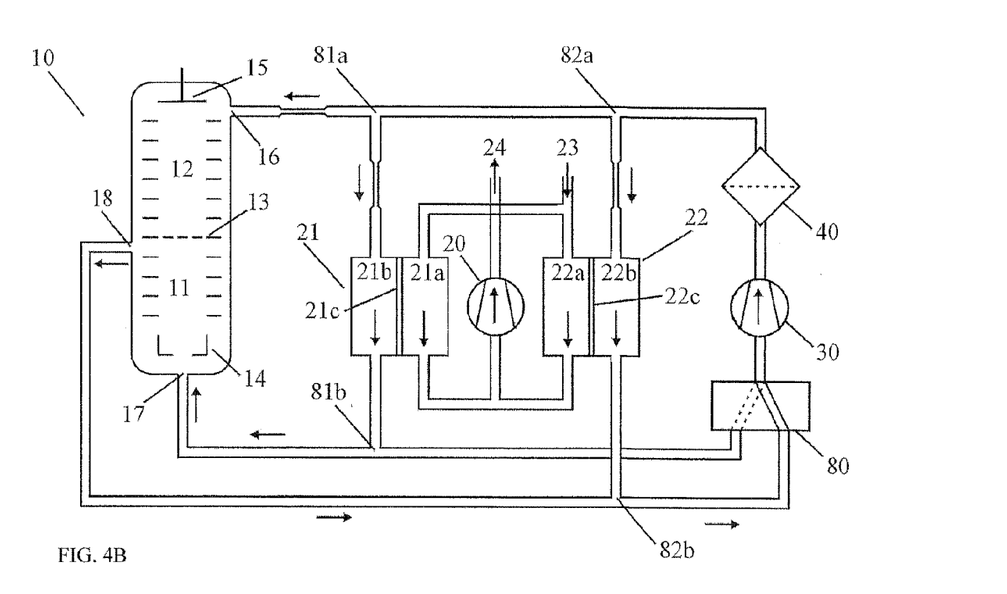

FIGS. 4A and 4B illustrate a fourth embodiment that switches between gas flows from two membrane inlets 21 and 22 of, for example, very different permeability to adapt sensitivity to analyte substance concentrations. The switching is performed by valve 80. In the present example, the two membranes 21c, 22c may have different areas, different thicknesses and/or may be comprised of different materials.

Figure 5A:
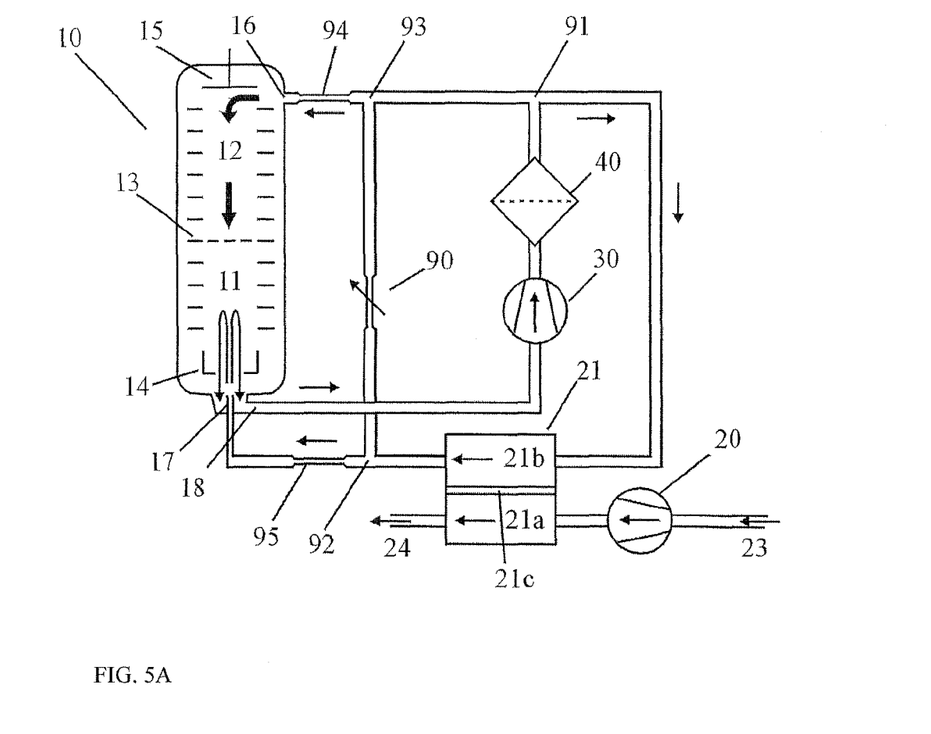
FIGS. 5A and 5B illustrate a fifth embodiment of the ion mobility spectrometer configured to adapt the monitoring process to changing analyte substance concentrations.
Figure 5B:
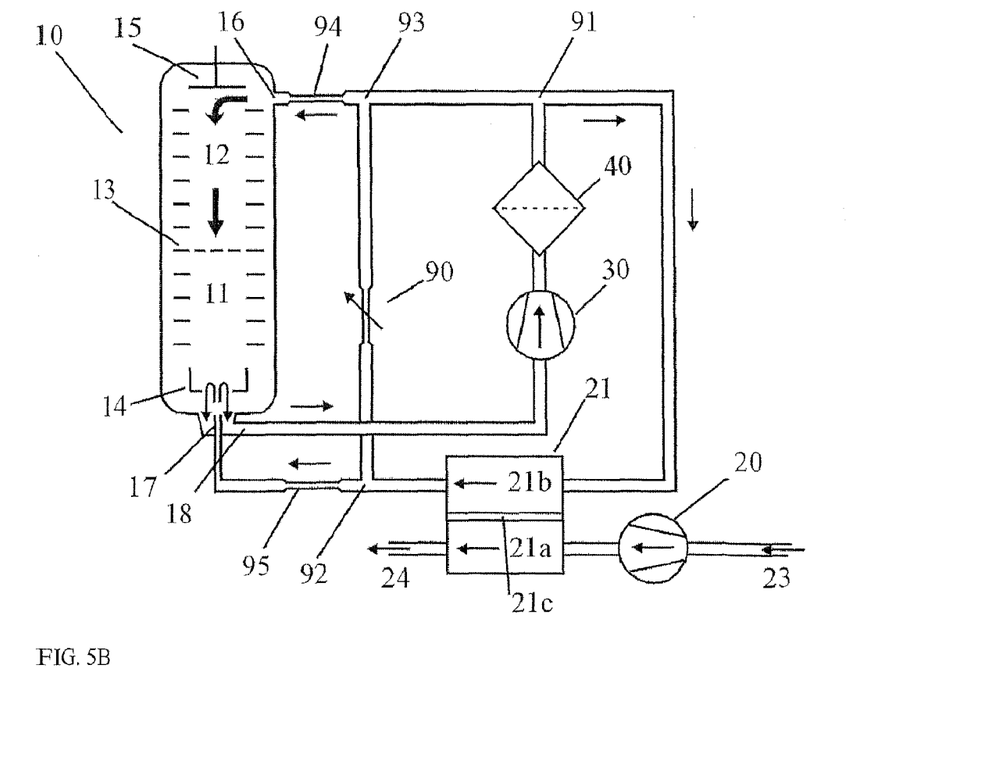

FIGS. 5A and 5B illustrate a fifth embodiment that guides the gas flow inside the reaction chamber on different paths, controlling the exposure of analyte substance molecules to protonating reaction ions. An inner gas connection 17 is formed as an inlet nozzle having a relatively small flow cross-section and extends into the reaction chamber 11. An analog valve 90 positioned in a side branch allows cleaned circulating gas from the pressure side of the gas pump 30 to be added to the analyte-containing circulating gas before it is fed through the gas connection 17 into the reaction chamber 11. As a result, the rate of the flow into the reaction chamber 11 and the concentration of the analyte substances changes. The analyte substances penetrate deeper into the reaction chamber 11 as circulating gas added from the side branch increase the inlet velocity, as illustrated by comparing FIGS. 5A (valve 90 open) and 5B (valve 90 closed). The analyte substances remain in the reaction chamber 11 long enough to become ionized through interactions with the reactant ions, despite drift gas flowing out of the drift chamber 12 in the opposite direction. The measuring range adapts to the particular substance concentration through a shorter residence time, where the amount of additional cleaned gas is reduced by the analog valve 90.

Figure 6A:
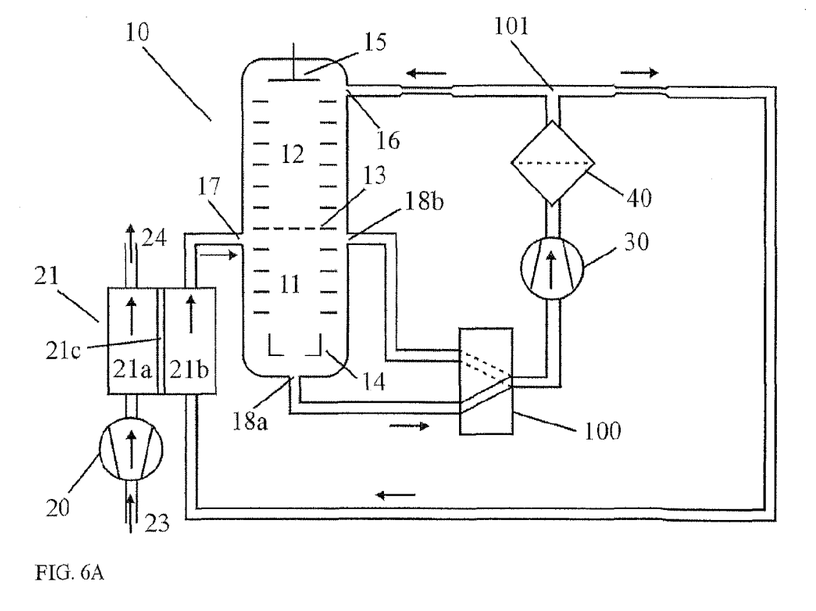
FIGS. 6A and 6B illustrate a sixth embodiment of the ion mobility spectrometer configured to expose analyte molecules differently to the ionizing reactant ions.
Figure 6B:
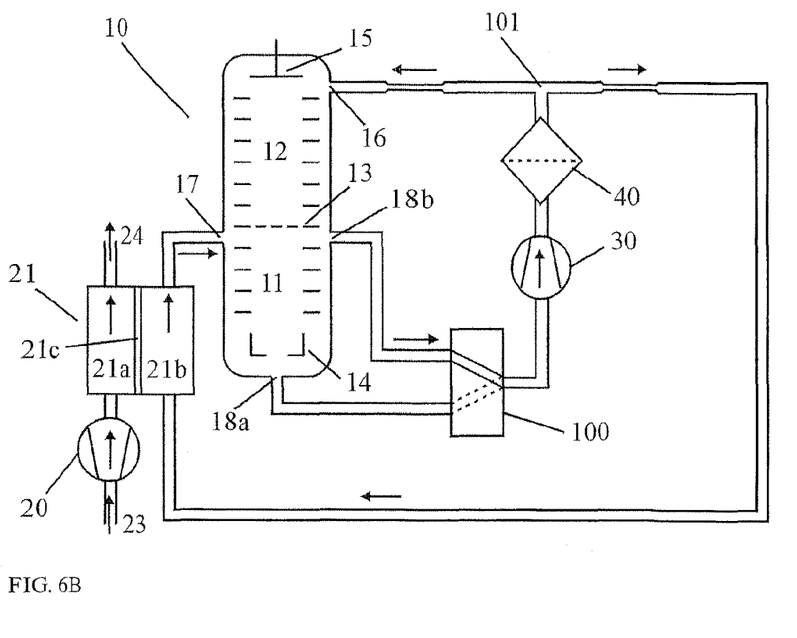

FIGS. 6A and 6B illustrate a sixth embodiment of an ion mobility spectrometer. Analyte-containing gas is siphoned from the reaction chamber 11 at one of two gas connections 18a or 18b, depending on the setting of a changeover valve 100. The gas connection 18b is positioned relatively close to the gas entrance 17. Gas connection 18a is positioned relatively far from the gas entrance 17 and relatively close to the radiation source 14. The analyte-containing circulating gas passes through the reaction chamber 11 along different paths and with different residence times, leading to a change in sensitivity and measuring range, due at least in part to the positioning of the two gas connections 18a and 18b. In some examples, the measuring tube of the ion mobility spectrometer has more than two gas outlets and/or more than one gas inlet.

This disclosure is not limited to drift-time ion mobility spectrometers, but can be advantageously employed with any ion mobility spectrometer that has a closed internal gas circuit. In addition, most embodiments may be operated as concentration-dependent ion mobility spectrometers, where the concentration of analyte substance flowing into the reaction chamber 11 is reduced by additional circuitry instead of the amount of the analyte substance.

Although the present invention has been illustrated and described with respect to several preferred embodiments thereof, various changes, omissions and additions to the form and detail thereof, may be made therein, without departing from the spirit and scope of the invention.

The invention claimed is:
1. A method, comprising:

supplying an analyte substance into a reaction chamber of an ion mobility spectrometer having a closed internal gas circuit and at least one membrane inlet having an inner membrane chamber;
changing at least one of flow resistances and gas paths in the closed internal gas circuit; and
controlling at least one of a quantity and a concentration of analyte-containing gas flowing from the inner membrane chamber to the reaction chamber.

2. The method of claim 1, further comprising:
changing least one of the quantity, the concentration and a dispersion of the analyte-containing gas; and
adapting the measuring range of the ion mobility spectrometer to change concentrations of the analyte substance in a sample gas.

3. The method of claim 2, wherein the changing of least one of the quantity, the concentration and the dispersion is controlled by feed-back from the result of an analytical measurement.

4. The method of claim 1, further comprising:
circulating analyte-containing gas from one of several membrane inlets to the reaction chamber during a metering mode; and
circulating analyte-containing gas from the other membrane inlets to a filter during an isolation mode.

5. The method of claim 4, further comprising:
switching the membrane inlets from the isolation mode to the metering mode at predetermined times and for predetermined periods; and
switching the membrane inlets from the metering mode to the isolation mode after each predetermined period.

6. The method of claim 1, further comprising:
automatically reversing a direction of the flow in the inner membrane chamber; and
preventing analyte-containing gas from flowing to the reaction chamber when a measurement signal from the ion mobility spectrometer exceeds a specified limit.

7. The method of claim 1, further comprising automatically reducing at least one of the quantity of gas or the concentration of analyte substances in the gas flowing to the reaction chamber and the dispersion of the analyte-containing gas inside the reaction chamber, to prevent a measurement signal from the ion mobility spectrometer from exceeding a specified limit.

8. The method of claim 1, further comprising diverting a controllable proportion of the analyte-containing gas to a filter through a branching point in the gas circuit between the inner membrane chamber and the reaction chamber.

9. The method of claim 1, further comprising:
introducing analyte-containing gas into the reaction chamber through at least one gas inlet;
removing the analyte-containing gas from the reaction chamber through at least one gas outlet; and
changing at least one of a quantity of the gas flowing in at least one of the gas inlets and a quantity of the gas flowing out of the gas outlets.

10. The method of claim 1, further comprising adding a controllable portion of cleaned circulating gas before the analyte-containing gas is fed into the reaction chamber.

11. An ion mobility spectrometer, comprising:
a measuring tube having a reaction chamber;
a transport system;
a filter coupled between the measuring tube and the transport system;
a membrane inlet having an inner membrane chamber coupled to the reaction chamber, the inner membrane chamber configured and positioned in a diagonal branch of a bridge circuit comprising at least a first and a second flow elements, where the flow resistance of at least one of the first and the second flow elements is controllable; and
where the measuring tube, the membrane inlet, the transport system, the bridge circuit and the flow elements define a closed internal gas circuit.

12. The ion mobility spectrometer of claim 11, wherein
the measuring tube further comprises a drift chamber;
the transport system is configured as a gas pump having a pressure side and a suction side;
the filter further comprises a first side and a second side, the first side is coupled to the pressure side of the gas pump, the second side is coupled to the drift chamber and a center connection of a changeover valve;
the reaction chamber is coupled to the suction side of the gas pump through a plurality of gas connections;
the inner membrane chamber of the membrane inlet is configured between the center connection of the changeover valve and the reaction chamber; and
the center connection is coupled to the suction side of the gas pump through at least one of a first flow element and a second flow element.

13. An ion mobility spectrometer, comprising:
a measuring tube having a reaction chamber;
a first membrane inlet having a first inner membrane chamber coupled to the reaction chamber through a first branching point;
a gas pump having a pressure side and a suction side, the pressure side is coupled to at least one of the measuring tube and the membrane inlet; and
at least one control element configured and positioned to have a variable flow resistance in a gas path from the first branching point to at least one of the pressure side and the suction side of the gas pump; and
where the measuring tube, the first membrane inlet, the gas pump and the control element define the closed internal gas circuit.

14. The ion mobility spectrometer of claim 13, wherein
the reaction chamber further comprises a first gas connection and a second gas connection, the first gas connection coupling the first inner membrane chamber and the reaction chamber, the second gas connection coupled to the suction side of the gas pump through a second branching point;
the measuring tube further comprises a drift chamber;
the pressure side of the gas pump is coupled to the first inner membrane chamber and the drift chamber through a filter; and
the first and the second branching points coupled together through a control element.

15. The ion mobility spectrometer of claim 13, wherein
the measuring tube further comprises a drift chamber;
the pressure side of the gas pump is coupled to the first inner membrane chamber and the drift chamber through a filter;
a second branching point is configured and positioned between the filter and the drift chamber;
the reaction chamber further comprises a first gas connection and a second gas connection, the first gas connection is coupled to the first inner membrane chamber through a third branching point, the second gas connection is coupled to the suction side of the gas pump and is positioned relatively close to the first gas connection; and
the second and the third branching points are coupled together through a control element.

16. The ion mobility spectrometer of claim 13, wherein the control element is at least one of an electrically controllable throttle valve and a combination of an electrically operated gas switching valve and a constant flow element.

17. The ion mobility spectrometer of claim 13, further comprises a second membrane inlet having an second inner membrane chamber, wherein
- the measuring tube further comprises a drift chamber;
- the pressure side of the gas pump is coupled to the drift chamber and the first inner membrane chambers through a filter, the inner membrane chambers configured in parallel;
- the reaction chamber further comprises a first and a second gas connection;
- the first inner membrane chamber is coupled to a first switch valve and the first gas connection;
- the second inner membrane chamber is coupled a second switch valve and the first gas connection; and
- the second gas connection is coupled to the reaction chamber and the first and the second switching valves, where the first and the second switching valves are coupled to the suction side of the gas pump.

18. The ion mobility spectrometer of claim 13, further comprises a second membrane inlet having an second inner membrane chamber, wherein
- the measuring tube further comprises a drift chamber;
- the pressure side of the gas pump is coupled to the drift chamber and the inner membrane chambers through a filter, the inner membrane chambers are configured in parallel;
- the reaction chamber further comprises a first and a second gas connection;
- the first inner membrane chamber is coupled to the first gas connection and to a first end connection of a changeover valve through a first branching point;
- the second inner membrane chamber is coupled to the second gas connection and a second end connection of the changeover valve through a second branching point; and
- the suction side of the gas pump is coupled to a center connection of the changeover valve.

19. An ion mobility spectrometer, comprising:
- a measuring tube having a reaction chamber, the reaction chamber includes at least one of a plurality of gas inlets and a plurality of gas outlets;
- a membrane inlet having an inner membrane chamber coupled to the reaction chamber through a branching point;
- a gas pump having a pressure side and a suction side, the pressure side coupled to at least one of the measuring tube and the membrane inlet;
- a control element configured and positioned within a close internal gas circuit to change a flow rate in at least one of the gas inlets and the gas outlets;
- at least one control element configured and positioned to have a variable flow resistance in a gas path from the branching point to at least one of the pressure side and the suction side of the gas pump; and
- where the measuring tube, the membrane inlet, the gas pump and the control element define the closed internal gas circuit.

20. The ion mobility spectrometer of claim 19, wherein at least one of the gas inlets and the gas outlets have a maximum possible distance between them.

* * * * *